United States Patent
Suzuki

(10) Patent No.: US 12,390,177 B2
(45) Date of Patent: Aug. 19, 2025

(54) PHOTON COUNTING X-RAY IMAGE DIAGNOSIS APPARATUS AND METHOD FOR GENERATING CALIBRATION DATA FOR PILEUP CORRECTION

(71) Applicant: CANON MEDICAL SYSTEMS CORPORATION, Otawara (JP)

(72) Inventor: Yojiro Suzuki, Oyama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 248 days.

(21) Appl. No.: 18/347,697

(22) Filed: Jul. 6, 2023

(65) Prior Publication Data

US 2024/0065654 A1 Feb. 29, 2024

(30) Foreign Application Priority Data

Aug. 24, 2022 (JP) .................................. 2022-133479

(51) Int. Cl.
*A61B 6/42* (2024.01)
*A61B 6/58* (2024.01)

(52) U.S. Cl.
CPC ............ *A61B 6/4241* (2013.01); *A61B 6/584* (2013.01); *A61B 6/585* (2013.01)

(58) Field of Classification Search
CPC ........ A61B 6/4241; A61B 6/584; A61B 6/585
See application file for complete search history.

(56) References Cited

U.S. PATENT DOCUMENTS

| | | | | |
|---|---|---|---|---|
| 2007/0076842 A1* | 4/2007 | Tkaczyk | ............... | A61B 6/4085 378/108 |
| 2007/0076848 A1* | 4/2007 | Walter | ................... | A61B 6/032 378/98.8 |
| 2008/0260094 A1* | 10/2008 | Carmi | .................. | A61B 6/4241 378/19 |
| 2009/0039273 A1* | 2/2009 | Tkaczyk | ................. | G01T 1/247 250/370.06 |
| 2011/0155899 A1* | 6/2011 | Dror | ....................... | G01T 1/171 250/252.1 |
| 2014/0105370 A1* | 4/2014 | Yamakawa | ............ | A61B 6/025 378/207 |

(Continued)

FOREIGN PATENT DOCUMENTS

JP 2014-158714 A 9/2014

*Primary Examiner* — Blake C Riddick
(74) *Attorney, Agent, or Firm* — Oblon, McClelland, Maier & Neustadt, L.L.P.

(57) ABSTRACT

A photon counting X-ray image diagnosis apparatus according to an embodiment includes an X-ray tube, a photon counting X-ray detector, and processing circuitry. Based on detection data sets obtained by performing a phantom imaging process using of mutually-different acquisition parameter sets by which X-rays radiated onto a phantom are detected by the X-ray detector, the processing circuitry identifies a boundary condition defining a range of acquisition parameter sets corresponding to a pileup occurrence. The processing circuitry sets a margin range based on the boundary condition. The processing circuitry generates acquisition parameter sets included in a range obtained by adding the margin range to the range of the acquisition parameter sets. The processing circuitry generates calibration data for a pileup correction based on detection data sets obtained by using the acquisition parameter sets.

10 Claims, 5 Drawing Sheets

(56) References Cited

U.S. PATENT DOCUMENTS

| | | | |
|---|---|---|---|
| 2014/0233693 A1 | 8/2014 | Wang et al. | |
| 2015/0160355 A1* | 6/2015 | Wang | G01N 23/046 378/207 |
| 2015/0198725 A1* | 7/2015 | Tamura | G01T 1/17 378/5 |
| 2015/0282778 A1* | 10/2015 | Kato | G06T 11/005 378/5 |
| 2015/0287221 A1* | 10/2015 | Takayama | G06T 11/005 378/91 |
| 2016/0095568 A1* | 4/2016 | Takanaka | A61B 6/54 378/111 |
| 2016/0113603 A1* | 4/2016 | Schirra | G01T 1/171 250/252.1 |
| 2016/0203620 A1* | 7/2016 | Zou | G06T 11/003 378/19 |
| 2016/0287205 A1* | 10/2016 | Zou | A61B 6/4266 |
| 2017/0119340 A1* | 5/2017 | Nakai | A61B 6/50 |
| 2017/0322319 A1* | 11/2017 | Iniewski | G01T 1/24 |
| 2017/0325756 A1* | 11/2017 | Teshigawara | A61B 6/037 |
| 2018/0204356 A1* | 7/2018 | Xia | A61B 6/582 |
| 2018/0211417 A1* | 7/2018 | Miyazaki | G01N 23/046 |
| 2018/0235562 A1* | 8/2018 | Petschke | A61B 6/4241 |
| 2019/0021685 A1* | 1/2019 | Kojima | A61B 6/4241 |
| 2020/0193654 A1* | 6/2020 | Yanoff | A61B 6/5258 |
| 2020/0222024 A1* | 7/2020 | Edic | G01N 23/046 |
| 2020/0323508 A1* | 10/2020 | Zhou | A61B 6/5205 |
| 2021/0113178 A1* | 4/2021 | Zhou | A61B 6/54 |
| 2021/0121142 A1* | 4/2021 | Kawata | G01T 7/005 |
| 2021/0121143 A1* | 4/2021 | Iniewski | A61B 6/585 |
| 2021/0186439 A1* | 6/2021 | Goederer | A61B 6/032 |
| 2021/0186440 A1* | 6/2021 | Kreisler | A61B 6/4241 |
| 2021/0236081 A1* | 8/2021 | Gebhardt | A61B 6/547 |
| 2021/0267562 A1* | 9/2021 | Carbonne Dit Leychert Garenne | A61B 6/582 |
| 2021/0401387 A1* | 12/2021 | Hupfer | G01T 1/17 |
| 2022/0057534 A1* | 2/2022 | Sundberg | A61B 6/5294 |
| 2022/0229196 A1* | 7/2022 | Zhan | A61B 6/035 |
| 2022/0395248 A1* | 12/2022 | Yokoi | A61B 6/585 |
| 2023/0293135 A1* | 9/2023 | Maltz | G01T 1/17 |
| 2023/0389883 A1* | 12/2023 | Fan | G01T 1/2964 |

* cited by examiner

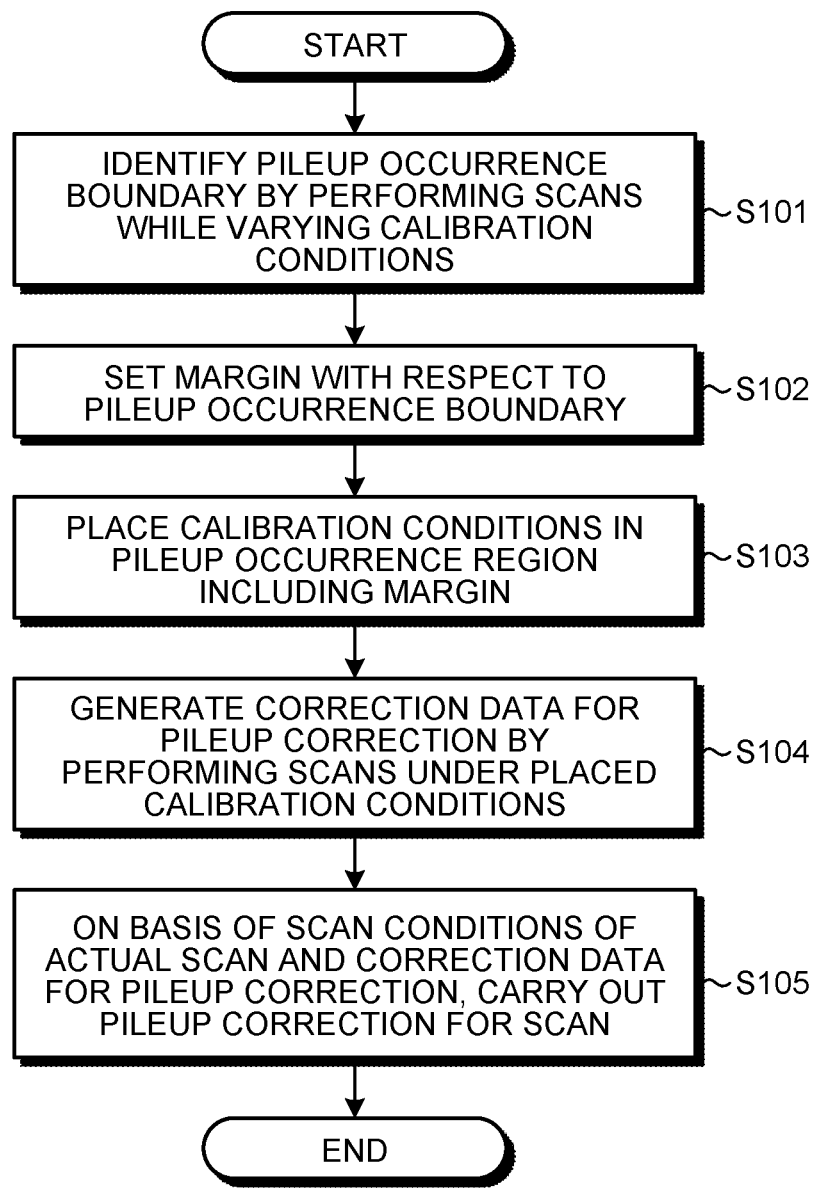

PHOTON COUNTING X-RAY IMAGE DIAGNOSIS APPARATUS AND METHOD FOR GENERATING CALIBRATION DATA FOR PILEUP CORRECTION

CROSS-REFERENCE TO RELATED APPLICATIONS

This application is based upon and claims the benefit of priority from Japanese Patent Application No. 2022-133479, filed on Aug. 24, 2022, the entire contents of which are incorporated herein by reference.

FIELD

Embodiments described herein relate generally to a photon counting X-ray image diagnosis apparatus and a method for generating calibration data for a pileup correction.

BACKGROUND

Conventionally, a Photon Counting Computed Tomography (PCCT) apparatus having a Photon Counting Detector (PCD) installed therein is known.

In the PCD, a pileup may occur when the radiation dose of incident X-rays is high, and there is a possibility that a measured count value may be different from a true count value. For this reason, by using calibration data for correcting such a pileup, a pileup correction may be performed in some situations so as to correct detector responses.

However, the calibration data for the pileup correction is generated, for example, on the basis of a plurality of pieces of acquisition data corresponding to a plurality of calibration conditions. In this situation, the calibration conditions include scan conditions such as radiation exposure amounts and X-ray tube voltage, as well as known water equivalent thicknesses of a phantom to be scanned. Accordingly, there is a problem where it would be necessary to perform a scan with respect to each of the plurality of calibration conditions, which would make the pileup correction inefficient.

BRIEF DESCRIPTION OF THE DRAWINGS

FIG. 8 is a flowchart illustrating an example of a pileup correcting process according to the embodiment.

DETAILED DESCRIPTION

Figure 1:
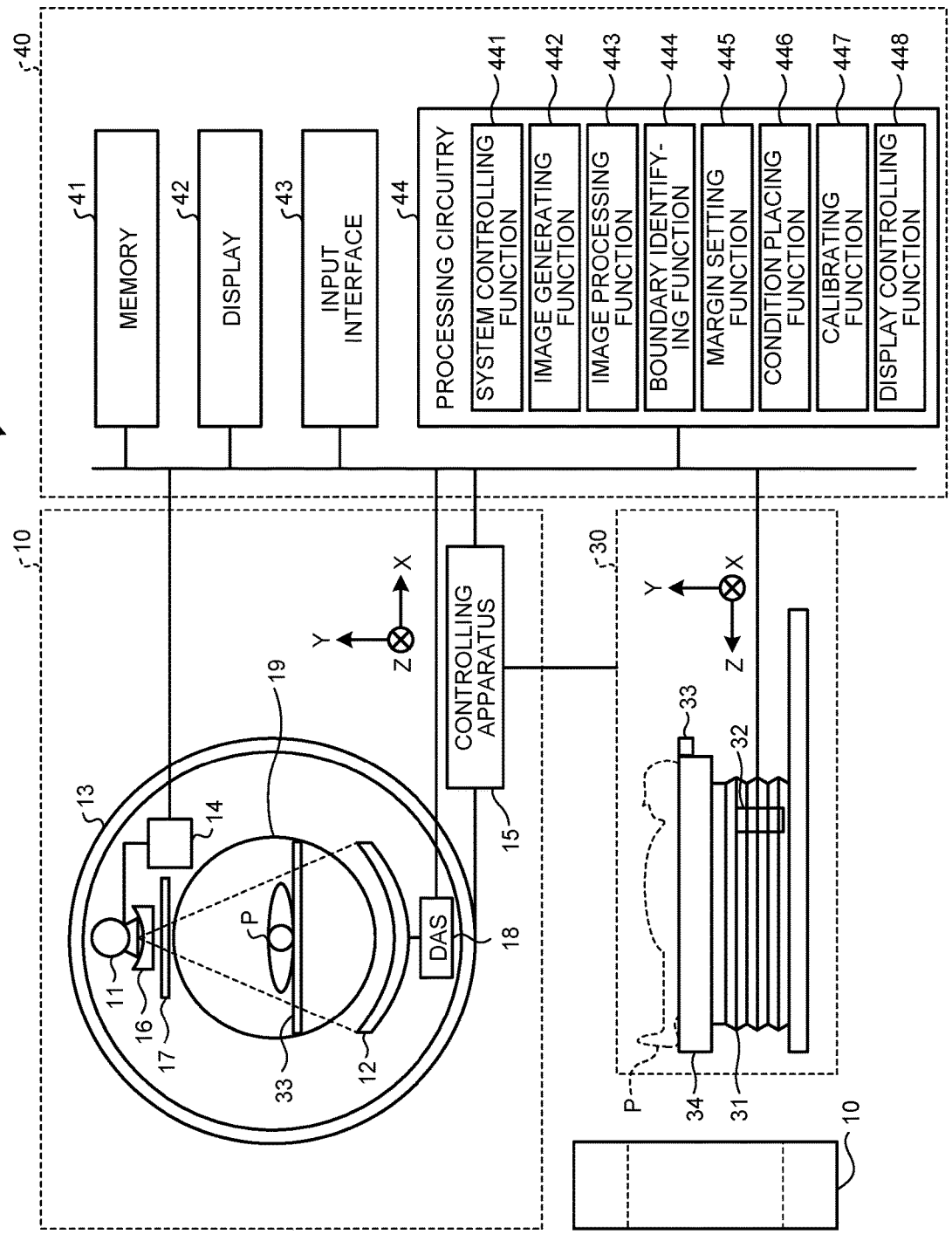
FIG. 1 is a diagram illustrating an exemplary configuration of an X-ray CT apparatus according to an embodiment.

One of the problems to be solved by the embodiments disclosed in the present specification and the like is to realize an efficient pileup correction for a photon counting X-ray image diagnosis apparatus. However, the problems to be solved by the embodiments disclosed in the present specification and drawings are not limited to the abovementioned problem. It is also possible to consider problems corresponding to the configurations in the embodiments described below as other problems.

A photon counting X-ray image diagnosis apparatus according to an embodiment includes an X-ray tube, a photon counting X-ray detector, and processing circuitry. The X-ray tube is configured to generate X-rays. The photon counting X-ray detector is configured to detect X-rays emitted from the X-ray tube. On the basis of a plurality of detection data sets obtained by performing a phantom imaging process using a plurality of mutually-different acquisition parameter sets by which X-rays radiated onto the phantom are detected by the photon counting X-ray detector, the processing circuitry is configured to identify a boundary condition defining a range of acquisition parameter sets corresponding to a pileup occurrence. The processing circuitry is configured to set a margin range based on the boundary condition. The processing circuitry is configured to generate a plurality of acquisition parameter sets included in a range obtained by adding the margin range to the range of the acquisition parameter sets. The processing circuitry is configured to generate calibration data for a pileup correction on the basis of a plurality of detection data sets obtained by using the plurality of acquisition parameter sets.

A photon counting X-ray image diagnosis apparatus according to an embodiment includes an X-ray tube to generate X-rays and a photon counting X-ray detector to detect X-rays emitted from the X-ray tube. The photon counting X-ray image diagnosis apparatus is configured to generate calibration data for a pileup correction used for correcting detection data obtained from an imaging process by which X-rays radiated onto an examined subject are detected by the photon counting X-ray detector. The photon counting X-ray image diagnosis apparatus includes processing circuitry. The processing circuitry is configured to obtain a first group of a plurality of acquisition parameter sets that is based on empirical information and is for generating the calibration data. The processing circuitry is configured to obtain first detection data by performing a phantom imaging process using the first group of the plurality of acquisition parameter sets to detect X-rays radiated onto the phantom while employing the photon counting X-ray detector. The processing circuitry is configured to generate the calibration data on the basis of the acquired first detection data. The processing circuitry is configured to generate a second group of a plurality of acquisition parameter sets that is used for the phantom imaging process and is for updating the generated calibration data on the basis of at least one selected from among the first detection data, an elapsed time period since the first detection data was acquired, and a use status since the first detection data was acquired. The first and the second groups of the plurality of acquisition parameter sets are each control parameter sets for the photon counting X-ray image diagnosis apparatus to obtain detection data by performing the phantom imaging process. In each of the first and the second groups of the plurality of acquisition parameter sets, one or more acquisition parameter sets corresponding to no pileup occurrence are partially excluded from a plurality of acquisition parameter sets which the photon counting X-ray image diagnosis apparatus is capable of setting, in such a manner that the larger the thickness of the phantom used at the time of obtaining the detection data is, the more acquisition parameter sets are excluded from the plurality of acquisition parameter sets which the photon counting X-ray image diagnosis apparatus is capable of setting.

A method for generating calibration data for a pileup correction according to an embodiment includes: identifying a boundary condition defining a range of acquisition parameter sets corresponding to a pileup occurrence, on the basis of a plurality of detection data sets obtained by performing a phantom imaging process using a plurality of mutually-different acquisition parameter sets by which X-rays radiated onto the phantom are detected by an X-ray detector; setting a margin range based on the boundary condition; generating a plurality of acquisition parameter sets included in a range obtained by adding the margin range to the range of the acquisition parameter sets; and generating the calibration data for the pileup correction on the basis of a plurality of detection data sets obtained by using the plurality of acquisition parameter sets.

A pileup correction calibration data generating method according to an embodiment is a method for generating calibration data for a pileup correction used for correcting detection data obtained from an imaging process by which X-rays radiated from an X-ray generating unit onto an examined subject in a photon counting X-ray image diagnosis apparatus are detected by a photon counting X-ray detector. The generating method includes: obtaining a first group of a plurality of acquisition parameter sets that is based on empirical information and is for generating the calibration data; obtaining first detection data by performing a phantom imaging process using the first group of the plurality of acquisition parameter sets to detect X-rays radiated onto the phantom while employing the photon counting X-ray detector; generating the calibration data on the basis of the acquired first detection data; and generating a second group of a plurality of acquisition parameter sets that is used for the phantom imaging process and is for updating the generated calibration data, on the basis of at least one selected from among the first detection data, an elapsed time period since the first detection data was acquired, and a use status since the first detection data was acquired. The first and the second groups of the plurality of acquisition parameter sets are each control parameter sets for the photon counting X-ray image diagnosis apparatus to obtain detection data by performing the phantom imaging process. In each of the first and the second groups of the plurality of acquisition parameter sets, one or more acquisition parameter sets corresponding to no pileup occurrence are partially excluded from a plurality of acquisition parameter sets which the photon counting X-ray image diagnosis apparatus is capable of setting, in such a manner that the larger the thickness of the phantom used at the time of obtaining the detection data is, the more acquisition parameter sets are excluded from the plurality of acquisition parameter sets which the photon counting X-ray image diagnosis apparatus is capable of setting.

In the following sections, exemplary embodiments of a photon counting X-ray image diagnosis apparatus and a method for generating calibration data for correcting pileups will be explained, with reference to the accompanying drawings. In the following explanations, some of the constituents having functions that are the same or substantially the same as those previously described in already-referenced drawings will be referred to by using the same reference characters, and duplicate explanations will be provided only when necessary. Further, a same element may be depicted in mutually-different sizes or scales among the drawings. Furthermore, from a viewpoint of ensuring legibility of the drawings, for example, the reference characters may be appended only to principal or representative constituent elements in the description of the drawings. Even some of the constituent elements having the same or substantially the same functions may not have reference characters in some situations.

The embodiments described below will present examples in which an information processing apparatus configured to realize a method for generating calibration data for a pileup correction and/or a pileup correcting method using the calibration data is installed in a photon counting X-ray image diagnosis apparatus which includes a Photon Counting Detector (PCD).

Further, although the embodiments described below will present a Photon Counting X-ray Computed Tomography (PCCT) apparatus as an example of the photon counting X-ray image diagnosis apparatus, possible embodiments are not limited to this example. The information processing apparatus according to any of the embodiments may be realized as being installed in other medical image diagnosis apparatuses besides X-ray CT apparatuses. In those situations, a processor installed in any of the medical image diagnosis apparatuses is capable of realizing a method for generating calibration data for a pileup correction according to the embodiments, by executing a program read from a Read Only Memory (ROM) or the like and loaded into a Random Access Memory (RAM). Examples of the other medical image diagnosis apparatuses may include various types of medical image diagnosis apparatuses such as an X-ray diagnosis apparatus, a Single Photon Emission Computed Tomography (SPECT) apparatus, a SPECT-CT apparatus in which a SPECT apparatus and an X-ray CT apparatus are integrally formed, a Positron Emission computed Tomography (PET) apparatus, and a PET-CT apparatus in which a PET apparatus and an X-ray CT apparatus are integrally formed. Further, as one of the other medical image diagnosis apparatuses, an X-ray diagnosis apparatus such as an X-ray rotation angiography apparatus may be used. In other words, for example, it is also acceptable to use an X-ray diagnosis apparatus implementing cone beam CT to acquire a projection X-ray image by rotating a C-arm, as another example of the other medical image diagnosis apparatuses besides X-ray CT apparatuses.

For example, there are various types of X-ray CT apparatuses such as third generation CT and fourth generation CT apparatuses. It is possible to apply any type to the present embodiments. The third generation CT denotes a Rotate/Rotate-type in which an X-ray tube and a detector integrally rotate around an examined subject. The fourth generation CT denotes Stationary/Rotate-Type in which, while a large number of X-ray detecting elements arrayed in a ring formation are fixed, only an X-ray tube rotates around an examined subject.

The information processing apparatuses according to the embodiments do not necessarily have to be installed in a medical image diagnosis apparatus such as an X-ray CT apparatus and may be realized as an independent apparatus by using a computer that includes, as hardware resources thereof, a processor such as a Central Processing Unit (CPU) and memory elements such as a Read Only Memory (ROM) and a Random Access Memory (RAM). In that situation, the processor installed in the computer is capable of realizing the calibration data generating method and/or the pileup correcting method according to any of the embodiments, by executing a program read from the ROM or the like and loaded into the RAM.

FIG. 1 is a diagram illustrating an exemplary configuration of an X-ray CT apparatus 1 serving as a photon counting X-ray image diagnosis apparatus according to an embodiment. The X-ray CT apparatus 1 is configured to cause X-rays to be emitted from an X-ray tube 11 onto an examined subject (hereinafter, "patient") P and to detect the emitted X-rays by using an X-ray detector 12. The X-ray CT apparatus 1 is configured to generate a CT image related to the patient P, on the basis of an output of the X-ray detector 12.

As illustrated in FIG. 1, the X-ray CT apparatus 1 includes a gantry 10, a table 30, and a console 40. For the sake of convenience in the explanations, FIG. 1 depicts the gantry 10 in multiple locations. The gantry 10 is a scan apparatus including a configuration for performing an X-ray CT imaging process on the patient P. The table 30 is a transport apparatus configured to determine the position of the patient P while the patient P undergoing the X-ray CT imaging process is placed thereon. The console 40 is a computer configured to control the gantry 10. For example, the gantry 10 and the table 30 are installed in a CT examination room, whereas the console 40 is installed in a control room positioned adjacent to the CT examination room. The gantry 10, the table 30, and the console 40 are connected in a wired or wireless manner so as to be able to communicate with one another.

The console 40 does not necessarily have to be installed in the control room. For example, the console 40 may be installed in the same room with the gantry 10 and the table 30. Alternatively, the console 40 may be incorporated in the gantry 10.

Further, in the present embodiment, a rotation axis of a rotating frame 13 in a non-tilt state or the longitudinal direction of a tabletop 33 of the table 30 is defined as a Z-axis direction, while an axial direction orthogonal to the Z-axis direction and parallel to a floor surface is defined as an X-axis direction, and an axial direction orthogonal to the Z-axis direction and perpendicular to the floor surface is defined as a Y-axis direction.

As illustrated in FIG. 1, the gantry 10 includes the X-ray tube 11, the X-ray detector 12, the rotating frame 13, an X-ray high-voltage apparatus 14, a controlling apparatus 15, a wedge 16, a collimator 17, and data acquisition circuitry (a Data Acquisition System (DAS)) 18.

The X-ray tube 11 is a vacuum tube including a negative pole (a filament) configured to generate thermo electrons and a positive pole (a target) configured to generate X-rays upon collisions of the thermos electrons thereon. By using high voltage supplied from the X-ray high-voltage apparatus 14, the X-ray tube 11 is configured to radiate the X-rays onto the patient P, by causing the thermos electrons to be emitted from the negative pole to the positive pole.

Possible hardware used for generating the X-rays is not limited to the X-ray tube 11. For example, in place of the X-ray tube 11, it is also acceptable to generate the X-rays by using a fifth generation scheme. The fifth generation scheme includes: a focus coil configured to converge electronic beams generated from an electron gun; a deflection coil configured to cause electromagnetic deflection; and a target ring covering a half of a circle around the patient P and configured to generate X-rays upon collisions of the deflected electron beams thereon. In this situation, the hardware configured to generate the X-rays is an example of an X-ray generating unit.

The X-ray detector 12 is a photon counting X-ray detector (PCD) configured to detect X-rays from the X-ray tube 11. The X-ray detector 12 is configured to detect the X-rays that were emitted from the X-ray tube 11 and have passed through the patient P and to output an electrical signal corresponding to the radiation amount of the detected X-rays to the DAS 18. For example, the X-ray detector 12 includes arrays of X-ray detecting elements in each of which a plurality of X-ray detecting elements are arranged in a channel direction along an arc while being centered on a focal point of the X-ray tube 11. For example, the X-ray detector 12 has a structure in which the plurality of arrays of X-ray detecting elements in the channel direction are arranged in a slice direction (column direction, row direction).

In an example, the X-ray detector 12 includes, for instance, a plurality of detector modules, a collimator module, a single bias voltage generating unit, a common electrode, and a conductor. The plurality of detector modules are arranged, for example, in the channel direction along an arc while being centered on the focal point of the X-ray tube 11.

In each of the plurality of detector modules, for example, electrodes are provided on facing planes of semiconductor crystals of cadmium telluride (CdTe), cadmium zinc telluride (CdZnTe or "CZT"), or the like, and an electric field is generated with application of bias voltage. In the X-ray detector 12, when the radiation is absorbed by the crystals, electron-hole pairs are generated. As a result of electrons moving to the positive pole side (the anode electrode (pixel electrode) side), and the holes moving to the negative pole side (the cathode electrode side), a signal is output.

Each of the plurality of detector modules is provided with a plurality of anode electrodes and a plurality of cathode electrodes. In each of the plurality of detector modules, a plane formed by the plurality of anode electrodes corresponds to an anode plane. In each of the plurality of detector modules, a plane formed by the plurality of cathode electrodes corresponds to a cathode plane.

The single bias voltage generating unit is configured to generate the bias voltage to be applied to between the cathode electrodes provided on the semiconductor crystal and the anode electrodes provided on the semiconductor crystal. The single bias voltage generating unit is realized as hardware by using a single high-voltage power source (a bias power source), for example. The common electrode is electrically connected to the single bias voltage generating unit, so as to extend in the channel direction. For example, the common electrode is realized by using a bus bar which is a conductive stick made of metal, for example. In the following sections, to explain a specific example, the common electrode will be referred to as a bus bar.

The conductor causes the bus bar to be electrically conductive with the cathode electrodes on the semiconductor crystal in each of the plurality of detector modules. Further, outputs of the plurality of anode electrodes may be put together as necessary, according to an image taking condition for the patient P or an instruction received from a user via an input interface 43. In the following sections, to explain a specific example, it is assumed that the outputs of the plurality of anode electrodes are processed as outputs respectively corresponding to pixels independently.

Each of the plurality of anode electrodes (hereinafter, "detecting elements") is configured to output one pulse of an electrical signal (an analog signal), every time an X-ray photon becomes incident thereto. It is possible to count the quantity of the X-ray photons that have become incident to each of the detecting elements, by counting the quantity of the electrical signal (pulses). Further, by performing various types of calculating process on the signal, it is possible to measure an energy value of the X-ray photons that caused the signal to be output.

In addition to the detecting elements described above, the X-ray detector 12 includes, for example, a plurality of Application Specific Integrated Circuits (ASICs) that are connected to the detecting elements and configured to count the X-ray photons detected by the detecting elements. The ASICs are configured to count the X-ray photons that have become incident to the detecting elements by measuring the "pulse quantities" output by the detecting elements. Further, the ASICs are configured to measure the energy values of the counted X-ray photons, by performing a calculating process based on each "pulse magnitude (electric charge amount)". Further, the ASICs are configured to output a result of counting the X-ray photons to the DAS 18, as digital data.

The collimator module includes collimator boards and a collimator frame. In the collimator module, to a plane facing the semiconductor crystal, a conductor is attached. The collimator boards are provided on the radiation incident plane side of the semiconductor crystal. The collimator boards are provided between any two anode electrodes and arranged in at least the channel direction. More specifically, the collimator boards are arranged on the X-ray incident side of the cathode electrodes. More specifically, the plurality of collimator boards are arranged along the channel direction while being positioned so as face each other via the semiconductor crystal between any two adjacently-positioned anode electrodes among the plurality of anode electrodes.

Further, the collimator boards may further have a plurality of scattered ray elimination parts arranged along the column direction (the slice direction) orthogonal to the channel direction. The collimator boards are configured by using X-ray blocking boards having a function of absorbing scattered X-rays, for example, and may be referred to as an anti-scatter grid (hereinafter, "ASG"). Further, depending on the dimension of the arrays, the ASG may be referred to as a one-dimensional collimator, a two-dimensional collimator, or simply a grid.

The collimator frame is configured to support the plurality of collimator boards. The collimator frame is configured to support the collimator boards while avoiding the radiation incident plane of the semiconductor crystal. At two ends, in terms of the column direction, of the collimator frame, bus bars may be provided. In this situation, the bus bars may be arranged between the collimator frame and the plurality of detector modules. Further, the bus bars may be provided at two ends, in terms of the column direction, of the semiconductor crystal while being out of contact with the semiconductor crystal.

For example, the X-ray detector 12 may be a detector of an indirect conversion type including the grid, a scintillator array, and an optical sensor array. The scintillator array includes a plurality of scintillators. The scintillators each include a scintillator crystal that outputs light in a light quantity corresponding to the amount of incident X-rays. The grid is arranged on a surface of the scintillator array positioned on the X-ray incident plane side and includes an X-ray blocking board having the function of absorbing the scattered X-rays. The grid may be referred to as a collimator (a one-dimensional collimator or a two-dimensional collimator). The optical sensor array has a function of converting the light from the scintillators into electrical signals corresponding to the light quantities. As the optical sensor, an Si-based photomultipliers (SiPM) may be used, for example.

The rotating frame 13 is an annular frame configured to support the X-ray tube 11 and the X-ray detector 12 so as to oppose each other and to cause the X-ray tube 11 and the X-ray detector 12 to rotate by employing the controlling apparatus 15 (explained later). At an opening part 19 of the rotating frame 13, a field of view (FOV) is set. For example, the rotating frame 13 is cast by using aluminum as a material. Further, in addition to the X-ray tube 11 and the X-ray detector 12, the rotating frame 13 may further support the X-ray high-voltage apparatus 14, the wedge 16, the collimator 17, the DAS 18, and the like. In addition, the rotating frame 13 may further support various other elements that are not illustrated in FIG. 1.

The X-ray high-voltage apparatus 14 includes a high-voltage generating apparatus and an X-ray controlling apparatus. The high-voltage generating apparatus includes electrical circuitry such as a transformer, a rectifier, and the like and is configured to generate the high voltage to be applied to the X-ray tube 11 and a filament current to be supplied to the X-ray tube 11. The X-ray controlling apparatus is configured to control output voltage corresponding to the X-rays to be emitted by the X-ray tube 11. The high-voltage generating apparatus may be of a transformer type or an inverter type. The X-ray high-voltage apparatus 14 may be provided on the rotating frame 13 within the gantry 10 or may be provided on a fixed frame (not illustrated) within the gantry 10. In this situation, the fixed frame is a frame configured to rotatably support the rotating frame 13.

The controlling apparatus 15 includes: a driving mechanism such as a motor and an actuator; and processing circuitry configured to control the driving mechanism and including a processor, a memory, and the like. The controlling apparatus 15 is configured to receive input signals from the input interface 43 and an input interface provided for the gantry 10 and to control operations of the gantry 10 and the table 30. Examples of the operation control exercised by the controlling apparatus 15 include control to rotate the rotating frame 13, control to tilt the gantry 10, and control to bring the table 30 into operation. In this regard, the control to tilt the gantry 10 is realized as a result of the controlling apparatus 15 rotating the rotating frame 13 on an axis parallel to the X-axis direction, according to inclination angle (tilt angle) information input through an input interface attached to the gantry 10. In this situation, the controlling apparatus 15 may be provided for the gantry 10 or may be provided for the console 40.

The wedge 16 is a filter for adjusting the X-ray amount emitted from the X-ray tube 11. More specifically, the wedge 16 is a filter configured to pass and attenuate the X-rays emitted from the X-ray tube 11 so that the X-rays emitted from the X-ray tube 11 onto the patient P has a predetermined distribution. For example, the wedge 16 may be a wedge filter or a bow-tie filter and is structured by processing aluminum or the like so as to have a predetermined target angle and a predetermined thickness.

The collimator 17 is configured to limit a radiation range of the X-rays that have passed through the wedge 16. The collimator 17 is configured to slidably support a plurality of lead plates blocking the X-rays and is configured to adjust the shapes of slits formed by the plurality of lead plates. In some situations, the collimator 17 may be referred to as an X-ray limiter.

The DAS 18 is configured to read, from the X-ray detector 12, electrical signals corresponding to the radiation amounts of the X-rays detected by the X-ray detector 12. The DAS 18 is configured to amplify the read electrical signals and to integrate (add up) the electrical signals over a view period and to thus acquire detection data having a digital value corresponding to the radiation amount of the X-rays over the view period. The detection data may be referred to as projection data. For example, the DAS 18 is realized by using an Application Specific Integrated Circuit (ASIC)

having installed therein a circuitry element capable of generating the projection data. The projection data is transferred to the console 40 via a contactless data transfer apparatus or the like. In this situation, the DAS 18 is an example of a detecting unit.

In this situation, the detection data generated by the DAS 18 is transmitted, via optical communication, from a transmitter provided on the rotating frame 13 and including a Light Emitting Diode (LED), to a receiver provided in a non-rotating part of the gantry 10 (e.g., the fixed frame; not illustrated in FIG. 1) and including a photodiode, so as to be further transferred to the console 40. The method for transmitting the detection data from the rotating frame 13 being a rotating part, to the non-rotating part of the gantry 10 is not limited to the optical communication described above. It is acceptable to adopt any method as long as the data is transferred in a contactless manner.

The table 30 is an apparatus on which the patient P to be scanned is placed and moved. The table 30 includes a base 31, a table driving apparatus 32, the tabletop 33, and a supporting frame 34. The base 31 is a casing configured to support the supporting frame 34 so as to be movable vertically. The table driving apparatus 32 is a driving mechanism configured to move the tabletop 33 over which the patient P is placed in the longitudinal direction of the tabletop 33. The table driving apparatus 32 includes a motor and an actuator or the like. The tabletop 33 is a board on which the patient P is placed. The tabletop 33 is provided on the top face of the supporting frame 34. The tabletop 33 is capable of projecting from the table 30 toward the gantry 10 to make it possible to image the whole body of the patient P. For example, the tabletop 33 is formed with Carbon Fiber Reinforced Plastic (CFRP) having excellent X-ray transmissibility and physical properties such as rigidity and strength. Further, for example, the tabletop 33 may be hollow inside. The supporting frame 34 is configured to support the tabletop 33 so as to be movable in the longitudinal direction of the tabletop 33. In addition to the tabletop 33, the table driving apparatus 32 may be configured to move the supporting frame 34 in the longitudinal direction of the tabletop 33.

The console 40 includes a memory 41, a display 42, the input interface 43, and processing circuitry 44. Data communication among the memory 41, the display 42, the input interface 43, and the processing circuitry 44 is performed via a bus, for example. Although the console 40 is described as being separate from the gantry 10, the gantry 10 may include the console 40 or one or more of the constituent elements of the console 40.

The memory 41 is realized, for example, by using a semiconductor memory element such as a ROM, a RAM or a flash memory, or a hard disk, an optical disc, or the like. For example, the memory 41 is configured to store therein the projection data and reconstructed image data. Further, for example, the memory 41 is configured to store therein various types of programs. Further, a save region of the memory 41 may be provided in the X-ray CT apparatus 1 or may be provided in an external storage apparatus connected via a network. The memory 41 is an example of a storage unit.

The display 42 is configured to display various types of information. For example, the display 42 is configured to display a medical image (a CT image) generated by the processing circuitry 44, a Graphical User Interface (GUI) used for receiving various types of operations from an operator, and the like. As the display 42, it is possible to use an arbitrary display of any of various types, as appropriate. For example, it is possible to use, as the display 42, a Liquid Crystal Display (LCD), a Cathode Ray Tube (CRT) display, an Organic Electroluminescence Display (OLED), or a plasma display.

In this situation, the display 42 may be provided in any location in the control room. Further, the display 42 may be provided for the gantry 10. In addition, the display 42 may be of a desktop type or may be configured by using a tablet terminal or the like capable of wirelessly communicating with the main body of the console 40. Furthermore, as the display 42, one or more projectors may be used. The display 42 is an example of a display unit.

The input interface 43 is configured to receive various types of input operations from the operator, to convert the received input operations into electrical signals, and to output the electrical signals to the processing circuitry 44. For example, the input interface 43 is configured to receive, from the operator, an acquisition condition used at the time of acquiring the projection data, a reconstruction condition used at the time of reconstructing a CT image, an image processing condition used at the time of generating a post-processing image from a CT image, and the like.

As the input interface 43, it is possible to use, for example, a mouse, a keyboard, a trackball, a switch, a button, a joystick, a touchpad, a touch panel display, and/or the like, as appropriate. Further, in the present embodiment, the input interface 43 does not necessarily have to include these physical operational component parts. For instance, possible examples of the input interface 43 include electrical signal processing circuitry configured to receive an electrical signal corresponding to an input operation from an external input mechanism provided separately from the apparatus and to output the electrical signal to the processing circuitry 44. Also, the input interface 43 may be provided for the gantry 10. Alternatively, the input interface 43 may be configured by using a tablet terminal or the like capable of wirelessly communicating with the main body of the console 40. The input interface 43 is an example of an input unit.

The processing circuitry 44 is configured to control operations of the entirety of the X-ray CT apparatus 1. As hardware resources thereof, the processing circuitry 44 includes a processor and one or more memory elements such as a ROM, a RAM, and/or the like. By employing the processor that executes programs loaded into a memory, the processing circuitry 44 is configured to execute, among others, a system controlling function 441, an image generating function 442, an image processing function 443, a boundary identifying function 444, a margin setting function 445, a condition placing function 446, a calibrating function 447, and a display controlling function 448. The processing circuitry 44 is an example of a processing unit.

By employing the system controlling function 441, the processing circuitry 44 is configured to control various types of functions of the X-ray CT apparatus 1, on the basis of input operations received from the operator via the input interface 43. For example, the system controlling function 441 is configured to control a CT scan performed by the gantry 10. The processing circuitry 44 is configured to obtain detection data obtained from the CT scan. In an example, the processing circuitry 44 is configured to obtain a plurality of detection data sets by performing a phantom imaging process while using a plurality of mutually-different calibration conditions (acquisition parameter sets). The phantom imaging process is performed by causing the X-ray detector 12 to detect the X-rays radiated onto a phantom. In this situation, the calibration conditions denote control parameter sets for the X-ray CT apparatus 1 to obtain detection data by performing the phantom imaging process. The processing circuitry 44 realizing the system controlling function 441 is an example of an obtaining unit.

By employing the image generating function 442, the processing circuitry 44 is configured to generate data obtained by performing pre-processing processes such as a logarithmic conversion process, an offset correction process, an inter-channel sensitivity correction process, a beam hardening correction, and/or the like, on the detection data output from the DAS 18. The processing circuitry 44 is configured to store the generated data into the memory 41. The data (the detection data) before the pre-processing processes and the data after the pre-processing processes may collectively be referred to as projection data in some situations. The processing circuitry 44 is configured to generate CT image data by performing a reconstructing process that uses a Filtered Backprojection (FBP) method or a successive approximation reconstruction method, on the generated projection data (the projection data after the pre-processing processes). The processing circuitry 44 is configured to store the reconstructed CT image data into the memory 41. The projection data generated from a counting result obtained in the photon counting CT contains information about energy of the X-rays that were attenuated by passing through the patient P. Accordingly, for example, the processing circuitry 44 is able to reconstruct X-ray CT image data corresponding to a specific energy component. Further, for example, the processing circuitry 44 is able to reconstruct X-ray CT image data corresponding to each of a plurality of energy components.

Further, by employing the image generating function 442, the processing circuitry 44 is capable of assigning tones corresponding to the energy components to pixels in the X-ray CT image data having the energy components and thereby generating image data in which a plurality of pieces of X-ray CT image data that are color-coded according to the energy components thereof are superimposed on one another. Further, for example, the processing circuitry 44 is capable of generating image data that makes it possible to identify a substance by using the k-absorption edge unique to the substance. Other examples of the image data generated by the processing circuitry 44 include monochrome X-ray image data, density image data, and effective atomic number image data.

By employing the image processing function 443, the processing circuitry 44 is configured, by using a publicly-known method, to convert the CT image data generated by the image generating function 442, into tomographic image data on an arbitrary cross-sectional plane or three-dimensional image data, on the basis of an input operation received from the operator via the input interface 43. For example, the processing circuitry 44 is configured to generate rendering image data in an arbitrary viewpoint direction, by performing three-dimensional image processing such as volume rendering, surface rendering, an image value projecting process, a Multi-Planar Reconstruction (MPR) process, or a Curved MPR (CPR) process on the CT image data. Alternatively, the process of generating the three-dimensional image data (i.e., volume data) such as the rendering image data in the arbitrary viewpoint direction may directly be performed by the image generating function 442. The processing circuitry 44 realizing the image generating function 442 and the image processing function 443 is an example of an image processing unit.

By employing the boundary identifying function 444, the processing circuitry 44 is configured to identify a pileup occurrence boundary. The pileup occurrence boundary represents a boundary condition defining a range of acquisition parameter sets corresponding to pileup occurrences. In an example, the processing circuitry 44 is configured to identify the pileup occurrence boundary on the basis of a plurality of detection data sets obtained by performing the phantom imaging process using a plurality of mutually-different acquisition parameter sets. The processing circuitry 44 realizing the boundary identifying function 444 is an example of an identifying unit.

By employing the margin setting function 445, the processing circuitry 44 is configured to set a margin range based on the pileup occurrence boundary. In an example, the processing circuitry 44 is configured to set the margin range on the side of the pileup occurrence boundary having acquisition parameter sets corresponding to no pileup occurrence, among a plurality of acquisition parameter sets which the X-ray CT apparatus 1 is capable of setting. In an example, the processing circuitry 44 is configured to determine the size of the margin range on the basis of at least one selected from among: individual fluctuations of the X-ray detector 12, chronological changes in responses, quantum noise in the X-ray generation, and charge sharing. The processing circuitry 44 realizing the margin setting function 445 is an example of a setting unit.

By employing the condition placing function 446, the processing circuitry 44 is configured to place calibration conditions (acquisition parameter sets) to obtain detection data for generating calibration data for a pileup correction. In an example, the processing circuitry 44 is configured to generate a plurality of acquisition parameter sets (calibration conditions) included in a range obtained by adding the margin range to a range of acquisition parameter sets corresponding to pileup occurrences. In other words, the calibration conditions are a result of partially excluding certain calibration conditions corresponding to no pileup occurrence, from the plurality of calibration conditions which the X-ray CT apparatus 1 is capable of setting. In an example, in a range that makes a larger contribution to images based on detection data resulting from the pileup correction, the processing circuitry 44 is configured to generate the acquisition parameter sets more densely than in the other ranges. In an example, in a range where a tendency of the pileup occurrence boundary changes, the processing circuitry 44 is configured to generate the acquisition parameter sets more densely than in the other ranges. In an example, the larger the thickness of the phantom used at the time of obtaining the detection data sets is, the more acquisition parameter sets are excluded by the processing circuitry 44 from the plurality of acquisition parameter sets which the X-ray CT apparatus 1 is capable of setting. The processing circuitry 44 realizing the condition placing function 446 is an example of a generating unit.

By employing the calibrating function 447, the processing circuitry 44 is configured to generate the calibration data for the pileup correction, on the basis of the plurality of detection data sets obtained by using the plurality of acquisition parameter sets generated by the condition placing function 446. The processing circuitry 44 realizing the calibrating function 447 is an example of a calibrating unit.

By employing the display controlling function 448, the processing circuitry 44 is configured to cause the display 42 to display images on the basis of various types of image data generated by the image processing function 443. The images displayed on the display 42 include a color image according to the embodiment. Further, the images displayed on the display 42 include a CT image based on CT image data, a cross-sectional image based on cross-sectional image data on an arbitrary cross-sectional plane, a rendering image in an arbitrary viewpoint direction based on rendering image data in the arbitrary viewpoint direction, and the like. Further, the images displayed on the display 42 include an image for displaying an operation screen and images for displaying notifications and alerts for the operator.

The functions 441 to 448 do not necessarily need to be realized by a single piece of processing circuitry. It is also acceptable to structure the processing circuitry 44 by combining together a plurality of independent processors, so that the functions 441 to 448 are realized as a result of the processors executing the programs. In this situation, the functions 441 to 448 may be realized as being distributed among or integrated into one or more pieces of processing circuitry, as appropriate.

Further, although the above description indicates that the plurality of functions are executed by the console 40 being a single console, it is also acceptable to have the plurality of functions executed by mutually-different consoles. For example, the console 40 may include, in a distributed manner, one or more of the functions of the processing circuitry 44, namely, the image generating function 442, the image processing function 443, the boundary identifying function 444, the margin setting function 445, the condition placing function 446, and the calibrating function 447.

Further, a part or all of the processing circuitry 44 may be included not only in the console 40, but also in an integration server configured to perform processes collectively on pieces of detection data obtained by a plurality of medical image diagnosis apparatuses.

Further, at least one selected from among the calibration data generating process, the post-processing processes, the pileup correcting process, and the display process may be performed by one of the console 40 and an external workstation. Alternatively, at least one of the processes may be performed simultaneously by both the console 40 and a workstation. As the workstation, it is possible to use, as appropriate, a computer or the like that includes, as hardware resources thereof, a processor realizing the functions corresponding to the processes and one or more memory elements such as a ROM, a RAM, and/or the like.

For reconstructing the X-ray CT image data, it is possible to adopt either of a full scan reconstruction scheme and a half scan reconstruction scheme. For example, by employing the image generating function 442, the processing circuitry 44 is configured to use projection data corresponding to a full circle around the patient P, i.e., 360 degrees, when using the full scan reconstruction scheme. In contrast, the processing circuitry 44 is configured to use projection data corresponding to "180 degrees+a fan angle" when using the half scan reconstruction scheme. In the following sections, to simplify the explanations, it will be assumed that the processing circuitry 44 adopts the full scan reconstruction scheme by which the reconstruction is performed by using the projection data corresponding to the full circle around the patient P, i.e., 360 degrees.

Further, the techniques according to the present embodiment are applicable to both an X-ray computed tomography apparatus of a single-X-ray-tube type and an X-ray computed tomography apparatus of a so-called multiple-X-ray-tubes type in which a plurality of pairs each made up of an X-ray tube and a detector are installed on an rotating ring.

Further, the techniques according to the present embodiment are also applicable to the X-ray CT apparatus 1 configured to perform imaging processes according to a dual energy scheme. In that situation, the X-ray high-voltage apparatus 14 is capable of alternately switching between energy spectrum levels of the X-rays emitted from the X-ray tube 11, by performing high-speed switching between two voltage values, for example. In other words, the X-ray CT apparatus 1 may be configured to be able to acquire the projection data in mutually-different acquisition views, while modulating the X-ray tube voltage with timing according to an X-ray tube voltage modulation control signal. By imaging a patient with mutually-different X-ray tube voltage levels, it is possible to enhance dark/light contrast of a CT image on the basis of energy transmissibility of substances corresponding to each of the X-ray energy spectra.

Further, the X-ray CT apparatus 1 according to the present embodiment may be structured as a standing CT apparatus. In that situation, instead of moving the tabletop 33, it will be sufficient to provide a patient supporting mechanism configured to support the patient P in a standing position and configured to be movable along a rotation axis of the rotating part of the gantry 10. Alternatively, the X-ray CT apparatus 1 according to the present embodiment may be structured as a movable CT apparatus in which the gantry 10 and the table 30 are movable.

Next, a method for generating the calibration data for the pileup correction that is realized by the X-ray CT apparatus 1 serving as a photon counting X-ray image diagnosis apparatus according to the present embodiment will be explained further in detail, with reference to drawings.

Identifying the Pileup Occurrence Boundary

Figure 2:
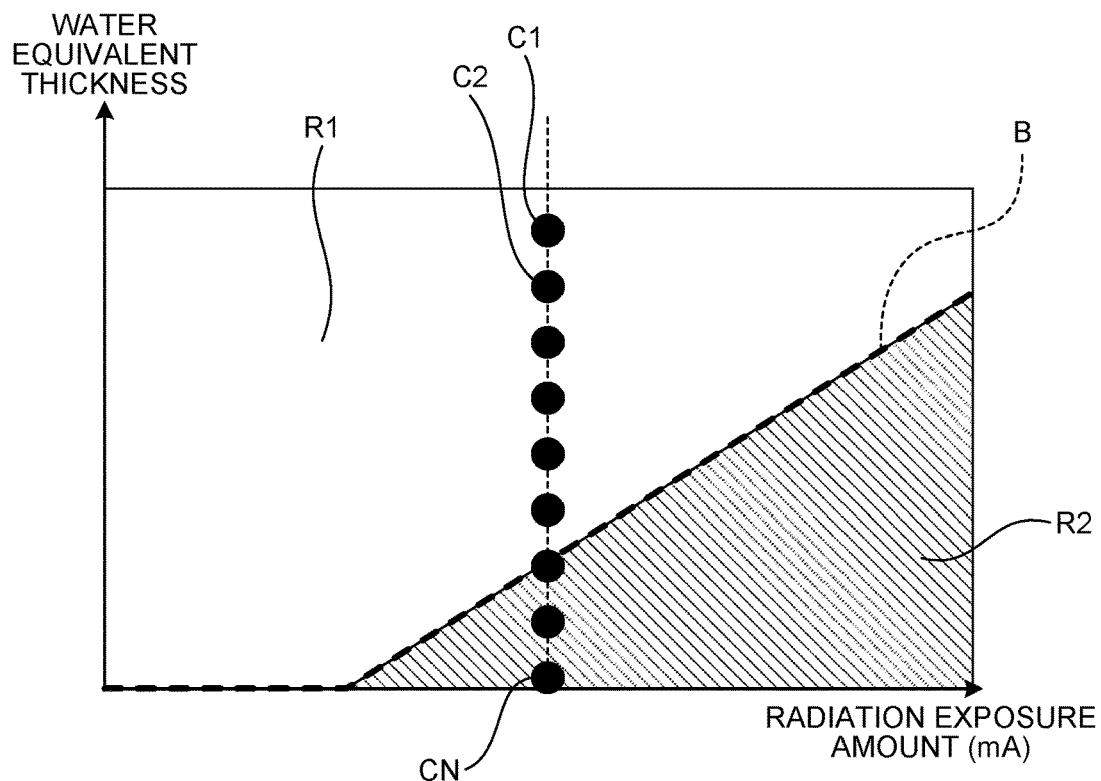
FIG. 2 is a chart for explaining a process of identifying a pileup occurrence boundary according to the embodiment.
Figure 3:
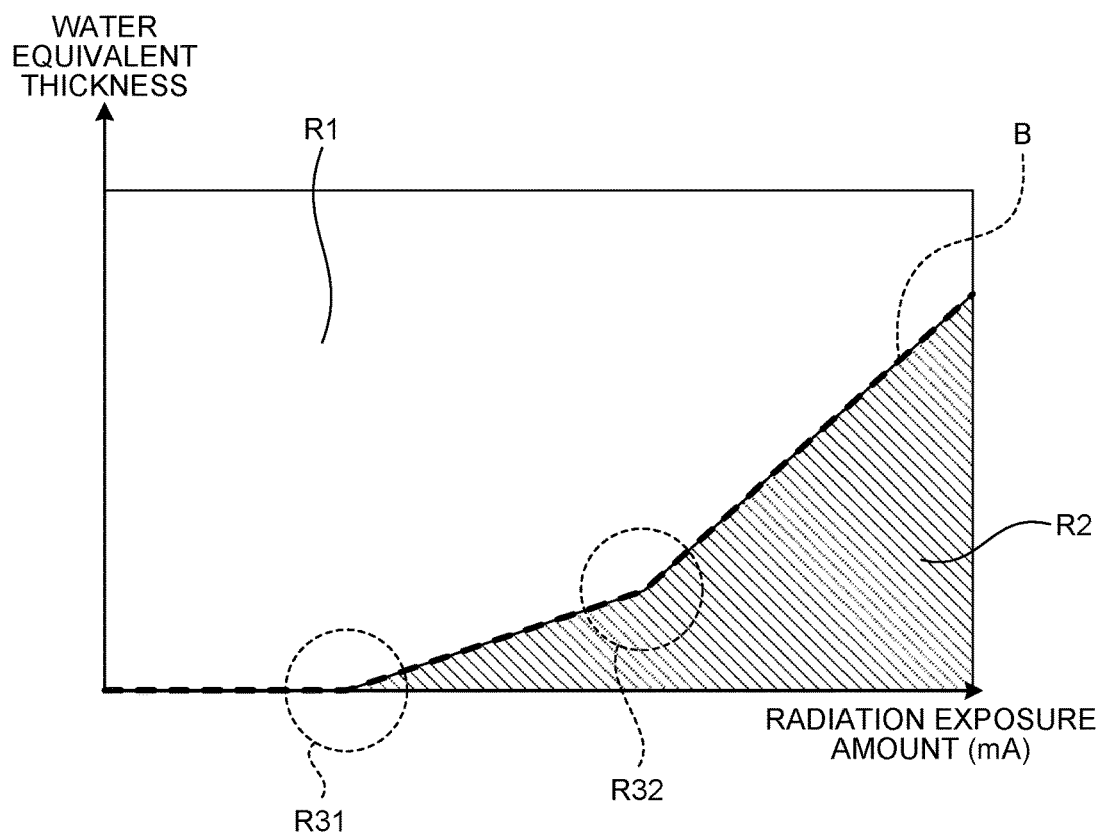
FIG. 3 is a chart for explaining a process of setting calibration conditions to be used for generating pileup correction data according to the embodiment.

FIGS. 2 and 3 are each a chart for explaining a process of identifying a pileup occurrence boundary B according to the embodiment. In the graphs in FIGS. 2 and 3, the vertical axis and the horizontal axis express water equivalent thicknesses ($\mu$) and radiation exposure amounts (mA), respectively.

In this situation, the radiation exposure amount serves as an example of scan conditions for a scan to obtain acquisition data and is represented by at least one value within the range which the X-ray CT apparatus 1 is capable of setting. Further, the water equivalent thickness is known information indicating a water equivalent thickness of the phantom used in the scan to obtain the calibration data. In the following sections, the scan to obtain the calibration data may be referred to as a phantom imaging process or a calibration scan.

In PCDs, when a photon incident speed is higher than a detector measuring speed, a pileup may occur, which is a phenomenon where linearity of inputs/outputs is lost. To cope with this phenomenon, a pileup correction is performed by performing scans under a plurality of scan conditions with respect to a plurality of phantoms corresponding to a plurality of water equivalent thicknesses so as to generate calibration data and further calibrating CT values by comparing obtained acquisition data with the calibration data (known information).

For example, the calibration data for the pileup correction may be a correction table generated by implementing a method such as a regression analysis or an Expectation-Maximization (EM) algorithm, while using a plurality of pieces of acquisition data obtained under the plurality of calibration conditions. In this situation, the calibration conditions include the scan conditions such as a radiation exposure amount and X-ray tube voltage and a known water equivalent thickness of the phantom to be scanned. In other words, the calibration data for the pileup correction is information indicating dependency of the water equivalent thickness on the radiation exposure amount.

However, when the calibration conditions include a condition where characteristics of the detector do not vary dependent on the radiation exposure amount, i.e., a condition under which no pileup occurs, it means that a calibration scan would be performed also for the calibration conditions in a region R1 corresponding to no pileup occurrence. In that situation, it would be necessary to perform a calibration scan with respect to each of the plurality of calibration conditions. Thus, a problem arises where the pileup correction including the calibration data generating process would be inefficient.

To cope with the circumstances described above, the process of generating the calibration data for the pileup correction according to the present embodiment includes identifying the pileup occurrence boundary B. For example, by employing the boundary identifying function 444, the processing circuitry 44 is configured to identify the pileup occurrence boundary B. As illustrated in FIG. 2, the pileup occurrence boundary B is a boundary between the region R1 having the calibration conditions corresponding to no pileup occurrence and a region R2 having the calibration conditions corresponding to pileup occurrences.

In an example, by employing the boundary identifying function 444, the processing circuitry 44 is configured to obtain a pileup occurrence boundary by monitoring count tendencies of the X-ray detector 12, while varying the radiation exposure amount and the water equivalent thickness. For example, as FIG. 2 illustrates examples of calibration conditions C (C1, C2, . . . and CN, where N is an arbitrary natural number), the processing circuitry 44 is configured to identify the pileup occurrence boundary B, by monitoring the count tendencies of the X-ray detector 12 with a plurality of water equivalent thicknesses with respect to an arbitrary radiation exposure amount. Alternatively, the processing circuitry 44 may identify the pileup occurrence boundary B, by monitoring the count tendencies of the X-ray detector 12 with a plurality of radiation exposure amounts with respect to an arbitrary water equivalent thickness.

In this situation, at the time of identifying the pileup occurrence boundary B, if the calibration scans were to be performed under a large number of calibration conditions, it means that a large number of calibration scans would also be performed for the calibration conditions in the region R1 corresponding to no pileup occurrence. To avoid this situation, by employing the boundary identifying function 444, the processing circuitry 44 is configured to perform a large number of calibration scans with respect to a pileup occurrence start region R31 and a region R32 where a tendency in the pileup occurrences changes, while performing an appropriate interpolation in the other parts.

Further, the processing circuitry 44 does not necessarily need to identify the pileup occurrence boundary B by using the acquisition data from the phantom imaging process and employing the boundary identifying function 444. Alternatively, the processing circuitry 44 may be configured to identify the pileup occurrence boundary B by using a simulation result based on measuring speed capabilities of the X-ray detector 12.

Setting the Margin Range

Figure 4:
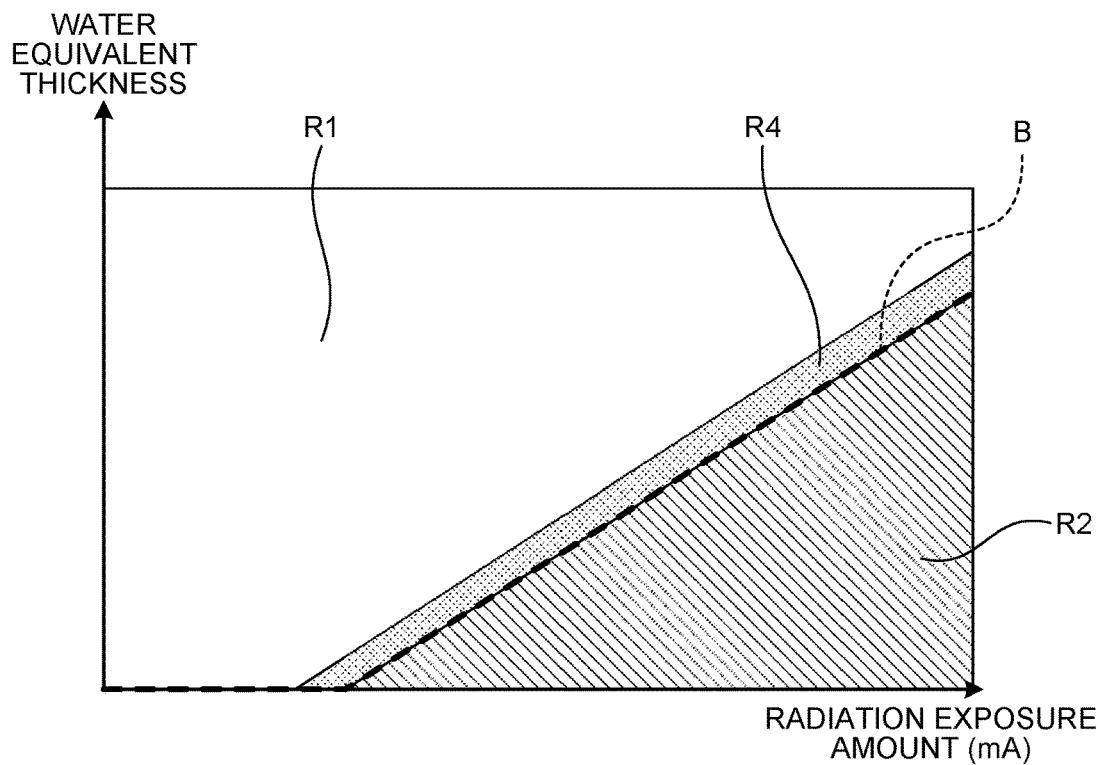
FIG. 4 is another chart for explaining the process of setting the calibration conditions to be used for generating the pileup correction data according to the embodiment.

FIG. 4 is a chart for explaining a process of setting the calibration conditions to be used for generating pileup correction data according to the embodiment. In the graph in FIG. 4, the vertical axis and the horizontal axis express water equivalent thicknesses and radiation exposure amounts (mA), respectively.

By employing the margin setting function 445, the processing circuitry 44 is configured to set a margin range R4 with respect to the identified pileup occurrence boundary B. The processing circuitry 44 is configured to set the margin range R4 on the side of the pileup occurrence boundary B where the region R1 corresponding to no pileup occurrence is positioned. The processing circuitry 44 is configured to determine the size of the margin range R4, on the basis of individual fluctuations of the X-ray detector 12, chronological changes in responses, quantum noise in the X-ray generation, impacts of charge sharing, and/or the like.

In this situation, the individual fluctuations of the X-ray detector 12 and the chronological changes in responses are determined, for example, on the basis of statistical values such as a median value or an average value related to variance among a plurality of scan sessions and variance among the plurality of detecting elements. In an example, it is also acceptable to determine, in advance, prescribed values (variance data) regarding variance in the individual fluctuations and the chronological changes in responses and to store the prescribed values in the memory 41 or the like. Further, the quantum noise of the X-ray generation is calculated on the basis of the radiation exposure amount (mA), for example. Furthermore, charging noise is calculated on the basis of geometry and/or the radiation exposure amount (mA) of the X-ray detector 12, for example.

In these situations, the size of the margin range R4 may be determined on the basis of the actual measurement values, may be determined on the basis of a simulation result, or may be determined on the basis of a combination of these.

Further, the size of the margin range R4 may be mutually the same among different radiation exposure amounts as illustrated in FIG. 4 or may be mutually different among the different radiation exposure amounts. In an example, with respect to the pileup occurrence start region R31 and the region R32 where the tendency in the pileup occurrences changes, the margin range R4 may be enlarged in comparison to the other regions.

Further, although the pileup occurrence boundary B is expressed with the single straight line in FIG. 4, possible embodiments are not limited to this example. For instance, as illustrated in FIG. 3, the pileup occurrence boundary B may be expressed with a combination of two or more straight lines.

Placement of the Calibration Conditions

Figure 5:
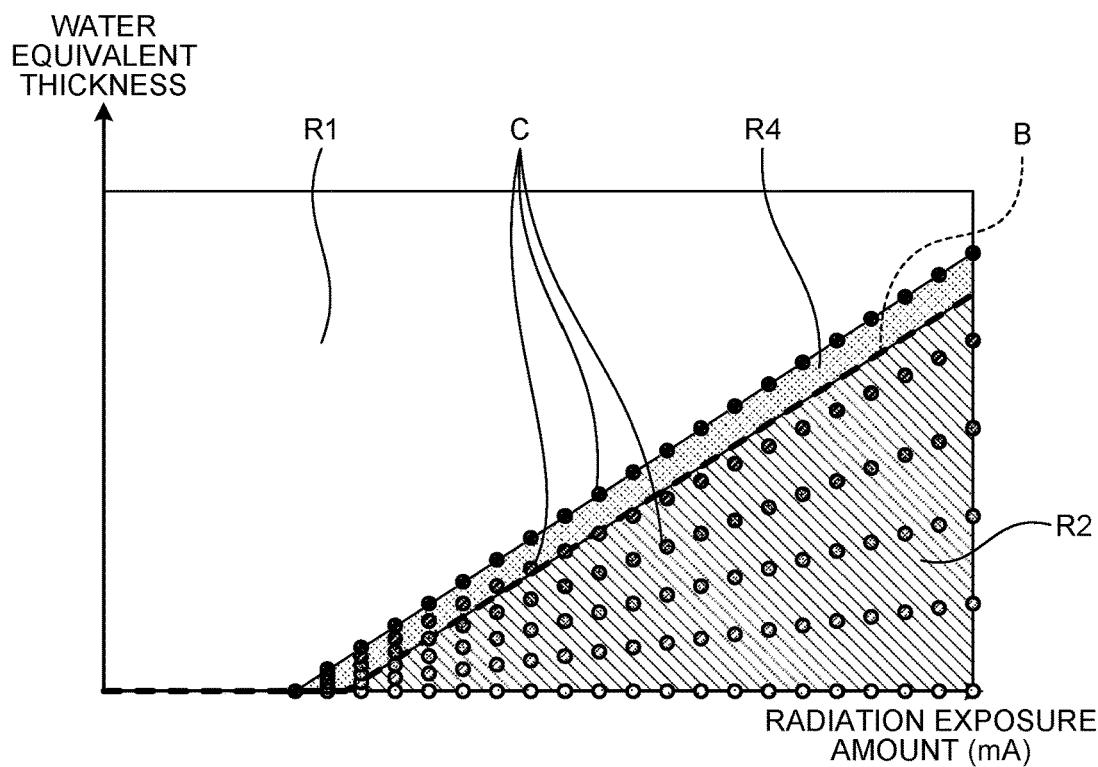
FIG. 5 is yet another chart for explaining the process of setting the calibration conditions to be used for generating the pileup correction data according to the embodiment.
Figure 6:
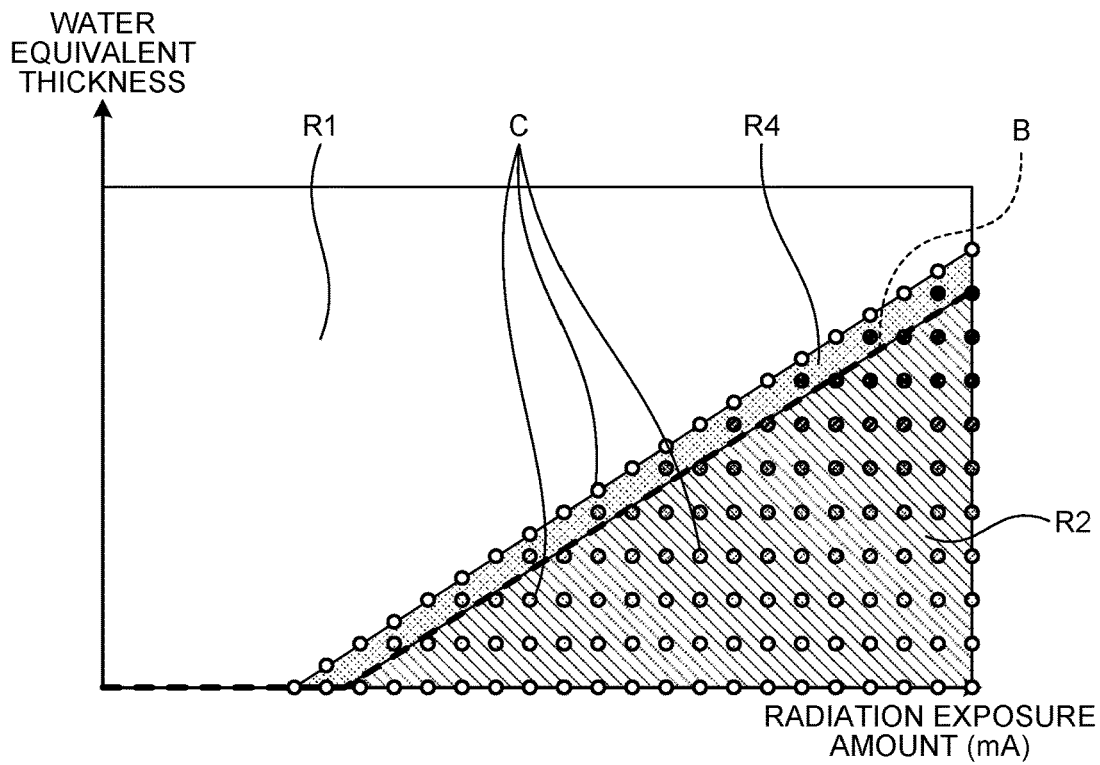
FIG. 6 is yet another chart for explaining the process of setting the calibration conditions to be used for generating the pileup correction data according to the embodiment.
Figure 7:
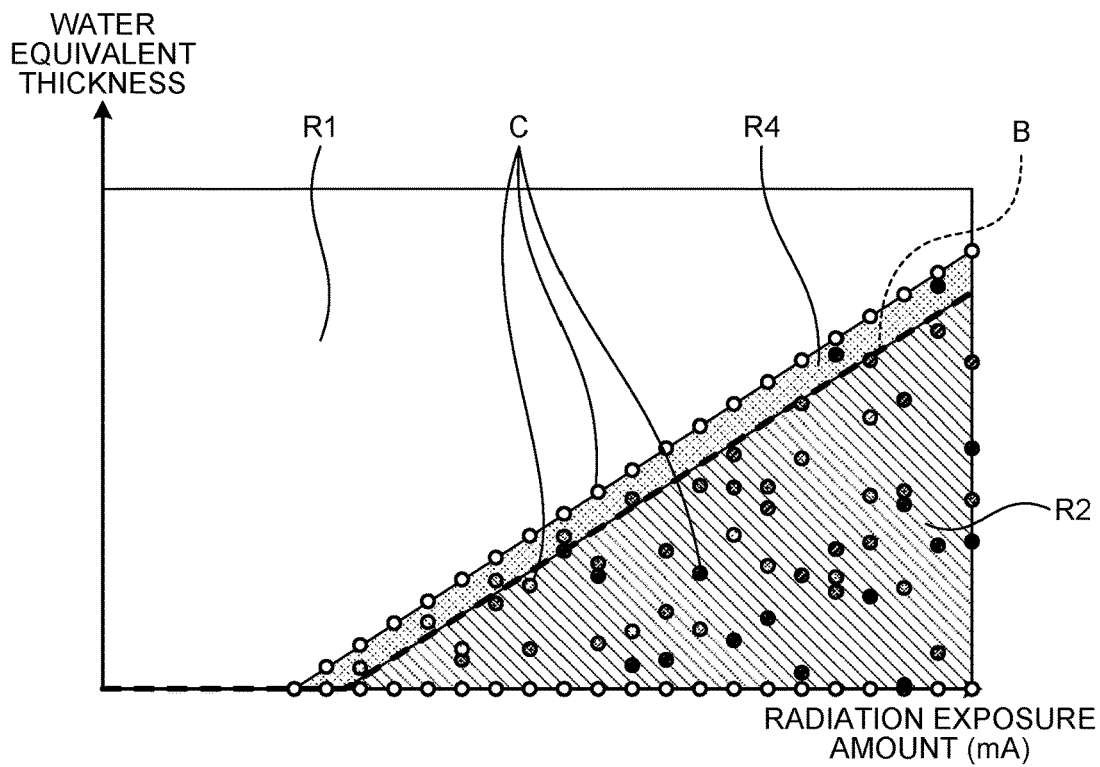
FIG. 7 is yet another chart for explaining the process of setting the calibration conditions to be used for generating the pileup correction data according to the embodiment.

FIGS. 5 to 7 are each a drawing for explaining the process of setting the calibration conditions used for generating the pileup correction data according to the embodiment. In the graphs in FIGS. 5 to 7, the vertical axis and the horizontal axis express water equivalent thicknesses and radiation exposure amounts (mA), respectively.

By employing the condition placing function 446, the processing circuitry 44 is configured to place the calibration conditions for the calibration scans, into the region obtained by adding the margin range R4 to the region R2 corresponding to pileup occurrences. As illustrated in FIGS. 5 to 7, in the placed calibration conditions (the plurality of acquisition parameter sets) for the calibration scans, the larger the thickness (the water equivalent thickness) of the phantom used at the time of obtaining the detection data set is, the more acquisition parameter sets are excluded from the plurality of acquisition parameter sets which the X-ray CT apparatus 1 is capable of setting.

By employing the condition placing function 446, the processing circuitry 44 is configured to place the calibration conditions C for the calibration scans, at least at a boundary (hereinafter, "first placement boundary") between the region R1 corresponding to no pileup occurrence and the margin range R4.

Further, by employing the condition placing function 446, the processing circuitry 44 is configured to place the calibration conditions C for the calibration scans at least at a boundary (hereinafter, "second placement boundary") corresponding to a zero (or minimum) water equivalent thickness within a periphery part of the region R2 corresponding to pileup occurrences.

In an example, by employing the condition placing function 446, the processing circuitry 44 may be configured, as illustrated in FIG. 5, to equally divide the space between the first placement boundary and the second placement boundary so as to place the calibration conditions C for the calibration scans at the division points (sampling points). In other words, the processing circuitry 44 may be configured to place an equal number of calibration conditions C with respect to each of the various radiation exposure amounts.

In another example, by employing the condition placing function 446, the processing circuitry 44 may be configured, as illustrated in FIG. 6, to divide the space between the first placement boundary and the second placement boundary in a mesh formation, so as to place the calibration conditions C for the calibration scans at the dividing points (sampling points). In other words, the processing circuitry 44 may be configured to place the calibration conditions C so that the sampling points are positioned at regular intervals.

In yet another example, by employing the condition placing function 446, the processing circuitry 44 may be configured, as illustrated in FIG. 7, to set the sampling points at random in the region between the first placement boundary and the second placement boundary so as to place the calibration conditions C for the calibration scans at the set sampling points.

In an example, by employing the condition placing function 446, the processing circuitry 44 is configured to change the placement density of the sampling points in accordance with degrees of contribution to images, within the region between the first placement boundary and the second placement boundary. More specifically, the processing circuitry 44 is configured to place the sampling points in such a manner that the higher a degree of contribution to the images is, the more densely the sampling points are placed. In this regard, in the examples in FIGS. 5 to 7, for instance, the degrees of contribution to images increase toward the bottom right of the graphs (i.e., larger radiation exposure amounts and smaller water equivalent thicknesses).

In an example, in the region between the first placement boundary and the second placement boundary, the processing circuitry 44 is configured, by employing the condition placing function 446, to place the sampling points more densely in the pileup occurrence start region R31 and in the region R32 where the tendency in the pileup occurrences changes, i.e., in the calibration condition ranges where the tendency of the pileup occurrence boundary B changes, than in the other regions.

Further, the aforementioned quantities of the sampling points to be placed are merely examples, and it is possible to determine the quantities as appropriate in accordance with required image quality and/or precision levels of interpolations.

Generating the Calibration Data

By employing the calibrating function 447, the processing circuitry 44 is configured to obtain the acquisition data, by performing the plurality of calibration scans under the plurality of calibration conditions placed in the region obtained by adding the margin range R4 to the region R2 corresponding to pileup occurrences. Further, the processing circuitry 44 is configured to generate the correction table (the calibration data) by implementing a method such as a regression analysis or an EM algorithm, while using the plurality of pieces of acquisition data obtained under the plurality of calibration conditions.

As for the calibration conditions, in place of or in addition to the radiation exposure amounts, it is acceptable to use X-ray tube voltage levels (kV), and/or combinations each made up of the type of the wedge 16 and a Field of View (FOV). In these situations also, similarly to the example described above, the pileup occurrence boundary B is identified while varying the X-ray tube voltage and/or the type of the wedge 16 and the FOV within the range which the X-ray CT apparatus 1 is capable of setting, so that the calibration conditions can be placed.

Further, the calibration data for the pileup correction may be generated in correspondence with each of the radiation exposure amounts, the water equivalent thicknesses, X-ray tube voltage levels, the combinations each made up of the type of the wedge 16 and an FOV, elements in the X-ray detector 12, channels in the X-ray detector 12, and/or segments of the X-ray detector 12.

Next, flows in a method for generating the calibration data for the pileup correction and a method for correcting pileups by using the calibration data which are realized by the X-ray CT apparatus 1 serving as a photon counting X-ray image diagnosis apparatus according to the embodiment will be explained further in detail, with reference to drawings.

FIG. 8 is a flowchart illustrating an example of a pileup correcting process according to the embodiment.

In an example, the method for generating the calibration data for the pileup correction is realized by a generating process performed by the X-ray CT apparatus 1. In an example, the pileup correcting method is realized by a correcting process performed by the X-ray CT apparatus 1.

By employing the boundary identifying function 444, the processing circuitry 44 identifies a pileup occurrence boundary by performing scans while varying the calibration conditions (step S101). More specifically, the processing circuitry 44 identifies the pileup occurrence boundary, by monitoring pileup occurrence statuses while varying the radiation exposure amount and the water equivalent thickness.

By employing the margin setting function 445, the processing circuitry 44 sets the margin range with respect to the identified pileup occurrence boundary (step S102).

By employing the condition placing function 446, the processing circuitry 44 places the calibration conditions in a pileup occurrence region including the margin range (step S103).

By employing the calibrating function 447, the processing circuitry 44 generates the correction data for the pileup correction, on the basis of the plurality of pieces of acquisition data corresponding to the obtained plurality of calibration conditions, by performing the scans under the placed calibration conditions (step S104).

For example, after the generating process (steps S101 through S104), the processing circuitry 44 performs an actual scan by employing the system controlling function 441.

By employing the calibrating function 447, the processing circuitry 44 performs the pileup correction on detection data (acquisition data) from the scan, on the basis of the scan conditions used in the actual scan and the correction data for the pileup correction (step S105).

Further, when the scan conditions of the actual scan do not match the calibration conditions, the processing circuitry 44 is configured to apply an interpolation based on a pileup correction table corresponding to the nearest calibration condition or a pileup correction table having at least one calibration condition in the surroundings.

In the present embodiment, an example was explained in which, after the generating process (steps S101 through S104), the scan and the correcting process for the scan (step S105) are performed; however, possible embodiments are not limited to this example. In another example, after the scan is performed, the generating process may be performed by using a plurality of pieces of acquisition data including the acquisition data obtained from the scan.

As explained above, according to the method for generating the calibration data for the pileup correction of the present embodiment, the pileup occurrence boundary is determined at first, so as to determine the calibration conditions, while also taking the various types of fluctuations into consideration. According to this configuration, there is no need to perform scans with respect to the region R1 corresponding to no pileup occurrence. It is therefore possible to generate the pileup correction table (the calibration data for the pileup correction) efficiently and effectively.

Generating the calibration data for the pileup correction efficiently and effectively contributes to performing the pileup correction efficiently and effectively. Further, according to the pileup correcting method using the calibration data of the present embodiment, it is possible to realize a calibration scheme that takes into consideration changes in detector responses to be caused by the pileups.

Further, there may be some situations where the pileup occurrence boundary B, the margin range R4, or the calibration conditions including these may be predetermined prior to the generating process. In an example, by employing the system controlling function 441, the processing circuitry 44 may obtain the predetermined calibration conditions from either the memory 41 or the outside of the X-ray CT apparatus 1. In this situation, the processing circuitry 44 realizing the system controlling function 441 is an example of an obtaining unit. Further, the predetermined calibration conditions serve as an example of the first group of a plurality of acquisition parameter sets that is based on empirical information and is for generating calibration data. In this situation, the empirical information may be information indicating calibration conditions obtained by the X-ray CT apparatus 1 in a previous generating process or may be information indicating a simulation result exhibiting a pileup occurrence status, individual fluctuations, and/or chronological changes in responses. Further, as the empirical information, calibration conditions related to another X-ray CT apparatus 1 may be used.

By employing the system controlling function 441, the processing circuitry 44 is configured to obtain detection data (the first detection data) by performing a phantom imaging process while using the predetermined calibration conditions. Further, by employing the calibrating function 447, the processing circuitry 44 is configured to generate the calibration data for the pileup correction by using the first detection data.

Further, by employing the condition placing function 446, the processing circuitry 44 is configured to generate a new set of calibration conditions (the second group of a plurality of acquisition parameter sets) on the basis of the first detection data. In this situation, the second group of the plurality of acquisition parameter sets are used in a new phantom imaging process for updating the generated calibration data. As a result, because the calibration conditions for the calibration scans are updated in accordance with the previous state of the calibration data, it is possible to enhance efficiency of the calibration data generating process.

Further, by employing the condition placing function 446, the processing circuitry 44 may generate a new set of calibration conditions (the second group of a plurality of acquisition parameter sets) on the basis of an elapsed time period since the first detection data was acquired and/or a use status since the first detection data was acquired, in place of or in addition to the first detection data. In other words, the calibration conditions may be changed in accordance with not only the previous state of the calibration data, but also the elapsed time period and/or the use status of the apparatus. With this arrangement, it is possible to generate appropriate calibration data and to thereby realize an appropriate pileup correction, even when sensor characteristics of the X-ray detector 12 change over the course of time.

Further, by employing the boundary identifying function 444 and the margin setting function 445, the processing circuitry 44 may update the pileup occurrence boundary B and the margin range R4 on the basis of the first detection data, at the time of generating the second group of the plurality of acquisition parameter sets.

The term "processor" used in the above explanations denotes, for example, a CPU, a Graphics Processing Unit (GPU), or circuitry such as an ASIC, a Programmable Logic device (PLD), or the like. Examples of the PLD include a Simple Programmable Logic Device (SPLD), a Complex Programmable Logic Device (CPLD), and a Field Programmable Gate Array (FPGA). The processor is configured to realize the functions by reading and executing the programs saved in the storage circuitry. The storage circuitry having the programs saved therein is a non-transitory computer-readable recording medium. In this situation, instead of saving the programs in the storage circuitry, it is also acceptable to directly incorporate the programs in the circuitry of the processor. In that situation, the processor is configured to realize the functions by reading and executing the programs incorporated in the circuitry thereof. Further, instead of executing the programs, it is also acceptable to realize the functions corresponding to the programs by using a combination of logical circuitry. Further, the processors in the present embodiments do not each necessarily have to be structured as a single piece of circuitry. It is also acceptable to structure one processor by combining together a plurality of pieces of independent circuitry so as to realize the functions thereof. Furthermore, it is also acceptable to integrate two or more of the constituent elements illustrated in FIG. 1 into a processor so as to realize the functions thereof.

According to at least one aspect of the embodiments described above, it is possible to realize the efficient pileup correction for the photon counting X-ray image diagnosis apparatus.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

In relation to the embodiments described above, the following notes are provided as certain aspects and selective characteristics of the present disclosure.

Note 1:

A photon counting X-ray image diagnosis apparatus including:
- an X-ray generating unit configured to generate X-rays;
- a photon counting X-ray detector configured to detect X-rays emitted from the X-ray generating unit; and
- an identifying unit configured to identify a boundary condition defining a range of acquisition parameter sets corresponding to a pileup occurrence, on the basis of a plurality of detection data sets obtained by performing a phantom imaging process using a plurality of mutually-different acquisition parameter sets by which X-rays radiated onto the phantom are detected by the photon counting X-ray detector;
- a setting unit configured to set a margin range based on the boundary condition;
- a generating unit configured to generate a plurality of acquisition parameter sets included in a range obtained by adding the margin range to the range of the acquisition parameter sets; and
- a calibrating unit configured to generate calibration data for a pileup correction on the basis of a plurality of detection data sets obtained by using the plurality of acquisition parameter sets.

Note 2:

The setting unit may be configured to set the margin range on a side of the boundary condition having acquisition parameter sets corresponding to no pileup occurrence.

Note 3:

The setting unit may be configured to determine the size of the margin range, on the basis of at least one selected from among: an individual fluctuation of the photon counting X-ray detector, a chronological change in a response, quantum noise in X-ray generation, and charge sharing.

Note 4:

In a range that makes a larger contribution to an image based on detection data resulting from the pileup correction, the generating unit may be configured to generate the acquisition parameter sets more densely than in other ranges.

Note 5:

In a range where a tendency of the boundary condition changes, the generating unit may be configured to generate the acquisition parameter sets more densely than in other ranges.

Note 6:

The larger the thickness of the phantom used at a time of obtaining the detection data sets is, the more acquisition parameter sets may be excluded by the generating unit from a plurality of acquisition parameter sets which the photon counting X-ray image diagnosis apparatus is capable of setting.

Note 7:

A photon counting X-ray image diagnosis apparatus that includes an X-ray generating unit to generate X-rays and a photon counting X-ray detector to detect X-rays emitted from the X-ray generating unit and that is configured to generate calibration data for a pileup correction used for correcting detection data obtained from an imaging process by which X-rays radiated onto an examined subject are detected by the photon counting X-ray detector, the photon counting X-ray image diagnosis apparatus including:
- an obtaining unit configured to obtain a first group of a plurality of acquisition parameter sets that is based on empirical information and is for generating the calibration data;
- an acquisition unit configured to obtain first detection data by performing a phantom imaging process using the first group of the plurality of acquisition parameter sets to detect X-rays radiated onto the phantom while employing the photon counting X-ray detector;
- a calibrating unit configured to generate the calibration data on the basis of the acquired first detection data; and
- a generating unit configured to generate a second group of a plurality of acquisition parameter sets that is used for the phantom imaging process and is for updating the generated calibration data on the basis of at least one selected from among the first detection data, an elapsed time period since the first detection data was acquired, and a use status since the first detection data was acquired, wherein
- the first and the second groups of the plurality of acquisition parameter sets are each control parameter sets for the photon counting X-ray image diagnosis apparatus to obtain detection data by performing the phantom imaging process, and
- in each of the first and the second groups of the plurality of acquisition parameter sets, one or more acquisition parameter sets corresponding to no pileup occurrence are partially excluded from a plurality of acquisition parameter sets which the photon counting X-ray image diagnosis apparatus is capable of setting, in such a manner that the larger the thickness of the phantom used at a time of obtaining the detection data is, the more acquisition parameter sets are excluded from the plurality of acquisition parameter sets which the photon counting X-ray image diagnosis apparatus is capable of setting.

Note 8:

The generating unit may be configured to generate the plurality of acquisition parameter sets in correspondence with at least one selected from radiation exposure amounts of the X-rays from the X-ray generating unit, X-ray tube voltage levels with which the X-rays are generated by the X-ray generating unit, and various types of wedges provided for the X-ray generating unit.

Note 9:

A method for generating calibration data for a pileup correction, the method including:
- identifying a boundary condition defining a range of acquisition parameter sets corresponding to a pileup occurrence, on the basis of a plurality of detection data sets obtained by performing a phantom imaging process using a plurality of mutually-different acquisition parameter sets by which X-rays radiated onto the phantom are detected by an X-ray detector;
- setting a margin range based on the boundary condition;
- generating a plurality of acquisition parameter sets included in a range obtained by adding the margin range to the range of the acquisition parameter sets; and
- generating the calibration data for the pileup correction on the basis of a plurality of detection data sets obtained by using the plurality of acquisition parameter sets.

Note 10:

A method for generating calibration data for a pileup correction used for correcting detection data obtained from an imaging process by which X-rays radiated from an X-ray generating unit onto an examined subject in a photon counting X-ray image diagnosis apparatus are detected by a photon counting X-ray detector, the method including:
- obtaining a first group of a plurality of acquisition parameter sets that is based on empirical information and is for generating the calibration data;
- obtaining first detection data by performing a phantom imaging process using the first group of the plurality of acquisition parameter sets to detect X-rays radiated onto the phantom while employing the photon counting X-ray detector;
- generating the calibration data on the basis of the acquired first detection data; and
- generating a second group of a plurality of acquisition parameter sets that is used for the phantom imaging process and is for updating the generated calibration data, on the basis of at least one selected from among the first detection data, an elapsed time period since the first detection data was acquired, and a use status since the first detection data was acquired, wherein
- the first and the second groups of the plurality of acquisition parameter sets are each control parameter sets for the photon counting X-ray image diagnosis apparatus to obtain detection data by performing the phantom imaging process, and
- in each of the first and the second groups of the plurality of acquisition parameter sets, one or more acquisition parameter sets corresponding to no pileup occurrence are partially excluded from a plurality of acquisition parameter sets which the photon counting X-ray image diagnosis apparatus is capable of setting, in such a manner that the larger the thickness of the phantom used at a time of obtaining the detection data is, the more acquisition parameter sets are excluded from the plurality of acquisition parameter sets which the photon counting X-ray image diagnosis apparatus is capable of setting.

What is claimed is:

1. A photon counting X-ray image diagnosis apparatus comprising:
   - an X-ray tube configured to generate X-rays;
   - a photon counting X-ray detector configured to detect X-rays emitted from the X-ray tube; and
   - processing circuitry configured, on a basis of a plurality of detection data sets obtained by performing a phantom imaging process using a plurality of mutually-different acquisition parameter sets by which X-rays radiated onto the phantom are detected by the photon counting X-ray detector, to identify a boundary condition defining a range of acquisition parameter sets corresponding to a pileup occurrence, to set a margin range based on the boundary condition, to generate a plurality of acquisition parameter sets included in a range obtained by adding the margin range to the range of the acquisition parameter sets, and to generate calibration data for a pileup correction on a basis of a plurality of detection data sets obtained by using the plurality of acquisition parameter sets.

2. The photon counting X-ray image diagnosis apparatus according to claim 1, wherein the processing circuitry is configured to set the margin range on a side of the boundary condition having acquisition parameter sets corresponding to no pileup occurrence.

3. The photon counting X-ray image diagnosis apparatus according to claim 1, wherein the processing circuitry is configured to determine a size of the margin range, on a basis of at least one selected from among: an individual fluctuation of the photon counting X-ray detector, a chronological change in a response, quantum noise in X-ray generation, and charge sharing.

4. The photon counting X-ray image diagnosis apparatus according to claim 1, wherein in a range that makes a larger contribution to an image based on detection data resulting from the pileup correction, the processing circuitry is configured to generate the acquisition parameter sets more densely than in other ranges.

5. The photon counting X-ray image diagnosis apparatus according to claim 1, wherein in a range where a tendency of the boundary condition changes, the processing circuitry is configured to generate the acquisition parameter sets more densely than in other ranges.

6. The photon counting X-ray image diagnosis apparatus according to claim 1, wherein the larger a thickness of the phantom used at a time of obtaining the detection data sets is, the more acquisition parameter sets are excluded by the processing circuitry from a plurality of acquisition parameter sets which the photon counting X-ray image diagnosis apparatus is capable of setting.

7. The photon counting X-ray image diagnosis apparatus according to claim 1, wherein the processing circuitry is configured to generate the plurality of acquisition parameter sets in correspondence with at least one selected from radiation exposure amounts of the X-rays from the X-ray tube, X-ray tube voltage levels with which the X-rays are generated by the X-ray tube, and various types of wedges provided for the X-ray tube.

8. A photon counting X-ray image diagnosis apparatus that includes an X-ray tube to generate X-rays and a photon counting X-ray detector to detect X-rays emitted from the X-ray tube and that is configured to generate calibration data for a pileup correction used for correcting detection data obtained from an imaging process by which X-rays radiated onto an examined subject are detected by the photon counting X-ray detector, the photon counting X-ray image diagnosis apparatus comprising:
   - processing circuitry configured: to obtain a first group of a plurality of acquisition parameter sets that is based on empirical information and is for generating the calibration data; to obtain first detection data by performing a phantom imaging process using the first group of the plurality of acquisition parameter sets to detect X-rays radiated onto the phantom while employing the photon counting X-ray detector; to generate calibrate the calibration data on a basis of the first detection data; and to generate a second group of a plurality of acquisition parameter sets that is used for the phantom imaging process and is for updating the generated calibration data on a basis of at least one selected from among the first detection data, an elapsed time period since the first detection data was acquired, and a use status since the first detection data was acquired, wherein
   - the first and the second groups of the plurality of acquisition parameter sets are each control parameter sets for the photon counting X-ray image diagnosis apparatus to obtain detection data by performing the phantom imaging process, and
   - in each of the first and the second groups of the plurality of acquisition parameter sets, one or more acquisition parameter sets corresponding to no pileup occurrence are partially excluded from a plurality of acquisition parameter sets which the photon counting X-ray image diagnosis apparatus is capable of setting, in such a manner that the larger a thickness of the phantom used at a time of obtaining the detection data is, the more acquisition parameter sets are excluded from the plurality of acquisition parameter sets which the photon counting X-ray image diagnosis apparatus is capable of setting.

9. A method for generating calibration data for a pileup correction, the method comprising:
- identifying a boundary condition defining a range of acquisition parameter sets corresponding to a pileup occurrence, on a basis of a plurality of detection data sets obtained by performing a phantom imaging process using a plurality of mutually-different acquisition parameter sets by which X-rays radiated onto the phantom are detected by an X-ray detector;
- setting a margin range based on the boundary condition;
- generating a plurality of acquisition parameter sets included in a range obtained by adding the margin range to the range of the acquisition parameter sets; and
- generating the calibration data for the pileup correction on a basis of a plurality of detection data sets obtained by using the plurality of acquisition parameter sets.

10. A method for generating calibration data for a pileup correction used for correcting detection data obtained from an imaging process by which X-rays radiated from an X-ray generating unit onto an examined subject in a photon counting X-ray image diagnosis apparatus are detected by a photon counting X-ray detector, the method comprising:
- obtaining a first group of a plurality of acquisition parameter sets that is based on empirical information and is for generating the calibration data;
- obtaining first detection data by performing a phantom imaging process using the first group of the plurality of acquisition parameter sets to detect X-rays radiated onto the phantom while employing the photon counting X-ray detector;
- generating the calibration data on a basis of the acquired first detection data; and
- generating a second group of a plurality of acquisition parameter sets that is used for the phantom imaging process and is for updating the generated calibration data, on a basis of at least one selected from among the first detection data, an elapsed time period since the first detection data was acquired, and a use status since the first detection data was acquired, wherein the first and the second groups of the plurality of acquisition parameter sets are each control parameter sets for the photon counting X-ray image diagnosis apparatus to obtain detection data by performing the phantom imaging process, and in each of the first and the second groups of the plurality of acquisition parameter sets, one or more acquisition parameter sets corresponding to no pileup occurrence are partially excluded from a plurality of acquisition parameter sets which the photon counting X-ray image diagnosis apparatus is capable of setting, in such a manner that the larger a thickness of the phantom used at a time of obtaining the detection data is, the more acquisition parameter sets are excluded from the plurality of acquisition parameter sets which the photon counting X-ray image diagnosis apparatus is capable of setting.

* * * * *